United States Patent
Takesako et al.

(10) Patent No.: US 6,239,297 B1
(45) Date of Patent: May 29, 2001

(54) SPHINGOSINE DERIVATIVES AND MEDICINAL COMPOSITION

(75) Inventors: Kazutoh Takesako, Otsu; Toru Kurome, Kusatsu; Naoyuki Awazu, Shiga; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/508,462

(22) PCT Filed: Sep. 11, 1998

(86) PCT No.: PCT/JP98/04093

§ 371 Date: Apr. 28, 2000

§ 102(e) Date: Apr. 28, 2000

(87) PCT Pub. No.: WO99/12890

PCT Pub. Date: Mar. 18, 1999

(30) Foreign Application Priority Data

Sep. 11, 1997 (JP) .................................................. 9-267965

(51) Int. Cl.$^7$ .................................................. C07C 233/00
(52) U.S. Cl. ........................... 554/58; 554/56; 554/103; 554/108; 514/613; 514/625; 514/626
(58) Field of Search ................................ 554/56, 58, 103, 554/108; 514/613, 625, 626

Primary Examiner—Deborah D. Carr
(74) Attorney, Agent, or Firm—Connolly, Bove, Lodge & Hutz, LLP.

(57) ABSTRACT

The present invention intends to provide a derivative of sphingosine analogue that is able to regulate the functions of sphigolipid, and its pharmaceutical compositions.

The present invention is the derivatives of sphingosine analogues represented by the general formula (I) described below.

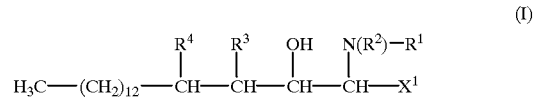

In the formula, $R^1$ and $R^2$, which are the same or different each other, are hydrogen, alkyl groups having 1–4 carbon atoms, or acyl groups having 2–5 carbon atoms. $R^3$ and $R^4$, which are the same or different each other, are hydrogen or hydroxyl groups; or $R^3$ and $R^4$ make up a covalent bond. $X^1$ is —$(CH_2)_n$—CO—NH—CH($R^5$)—$R^6$ or —$(CH_2)_m$—O—CO—CH($R^7$)—$R^8$.

2 Claims, No Drawings

SPHINGOSINE DERIVATIVES AND MEDICINAL COMPOSITION

This application is a 371 of PCT/JP98/04095 filed Sep. 11, 1998.

TECHNICAL FIELD

The present invention relates to derivatives of sphingosine analogues and their pharmaceutical compositions, which are useful as drugs for the treatment of fungal infections, allergic diseases, immune disorders, etc.

PRIOR ART

Sphingosine is a compound having the chemical structure shown in the general formula described below, in which $Y^1$ is hydrogen. It is known that various sphingolipids having sphingosine as a constituent are widely distributed in the living body including on the surface of cell membranes of cells in the nervous system. Also we know glycosphingolipids, which have one or several kinds of sugars as $Y^1$ via a glycoside bond linked to a ceramide having a fatty acid bound to the amino group of sphingosine via a peptide bond, and sphingophospholipids, including sphingomyelin, which have a phosphoric acid and a base such as choline or ethanolamine as $Y^1$ linked to the above-mentioned ceramide.

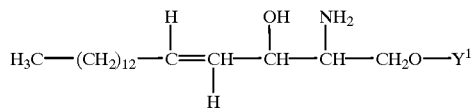

A sphingolipid is one of the lipids having important roles in the living body. We know a disease called lipidosis which is caused by accumulation of a specified sphingolipid in the body concomitant with the abnormalities in the metabolic pathways due to defect of an enzyme and others. Attractive effects of sphingolipids present on the cell membranes include functions in the regulation of cell growth and discrimination of each cell; functions in the developments and differentiation; functions in nerves; involvement in the infections and malignancy of cells; and others. Lots of physiological roles of such effects remain to be solved. Recently a possibility that ceramide, a derivative of sphingosine, has an important role in the mechanism of cell signal transduction was indicated, and studies about its effects and so forth on apoptosis and cell cycle have been actively performed.

Fungi and plants have sphingolipids and the major sphingosine contained in these organisms has the formula described below. It is known that these lipids have important roles in the cell growth of fungi and plants, but details of the roles remain to be solved.

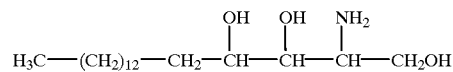

Recently it has been known that derivatives of sphingolipids and their related compounds exhibit a variety of biological activities through inhibition or stimulation of the metabolism pathways. These compounds include inhibitors of protein kinase C, inducers of apoptosis, immunosuppressive compounds, antifungal compounds, and the like. Substances having these biological activities are expected to be useful compounds for various diseases.

SUMMARY OF THE INVENTION

In view of the above present states, the present invention intends to provide a derivative of sphingosine analogue that is able to regulate the functions of sphigolipid, and its pharmaceutical compositions.

In the course of a search for novel biologically active compounds, the inventors discovered novel biologically active compounds TKR1785's, which showed antifungal activity and immunosuppressive activity, in the culture broth of TKR1785 strain belonging to Penicillium sp.

In this specification, TKR1785's are compounds shown in the following general formula (II). TKR1785's described above include TKR1785-I shown as the following formula (IIa) and TKR1785-II (IIb).

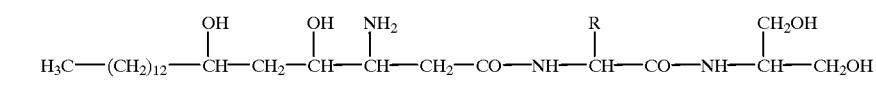

(In the formula, R represents CH(CH$_3$)$_2$ or CH(CH$_3$)C$_2$H$_5$)

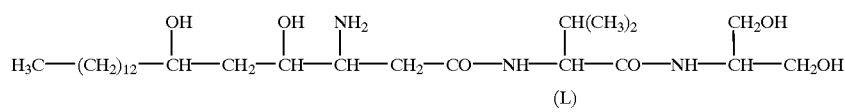

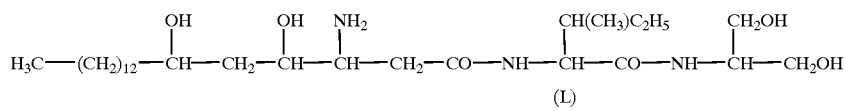

The inventors succeeded in preparation of novel sphingosine analogues represented by the following formula (III) by hydrolysis of TKR1785's described above.

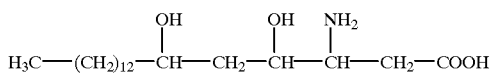

(III)

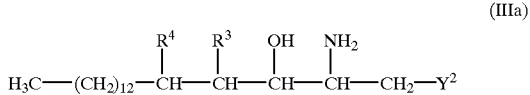

(IIIa)

Furthermore they succeeded in synthesis of peptide derivatives described in the following general formula (Ia) using, as the starting material, the compound described by the above formula (III) or the compound described by the following formula (IIIa) that was prepared from the compound described by the above formula (III) used as the starting material. They found that these compounds showed biological activities such as antifungal activity and immunosuppressive activity.

In the formula, $R^3$ and $R^4$, which are the same or different each other, are hydroxyl groups or hydrogen; or $R^3$ and $R^4$ make up a covalent bond. $Y^2$ is —COOH or —$CH_2OH$.

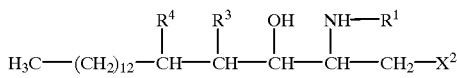

(Ia)

In the formula, $R^1$ is hydrogen, an alkyl group having 1–4 carbon atoms, or an acyl group having 2–5 carbon atoms. $R^3$ and $R^4$, which are the same or different each other, are hydrogen or hydroxyl groups; or $R^3$ and $R^4$ make up a covalent bond. $X^2$ is —CO—NH—CH($R^5$)—$R^6$ or —$CH_2$—O—CO—CH($R^7$)—$R^8$. $R^5$ is hydrogen, a hydroxyl group, or an alkyl group having 1–4 carbon atoms which may have a hydroxyl group. $R^6$ is —$CH_2OH$, —COOH, —$CONH_2$, or —CO—NH—CH($R^9$)—$R^{10}$. $R^9$ is hydrogen, a hydroxyl group, or an alkyl group having 1–4 carbon atoms which may have a hydroxyl group. $R^{10}$ is —$CH_2OH$, —COOH, —$CONH_2$, or —CO—NH—CH($R^{11}$)—$R^{12}$. $R^{11}$ is hydrogen, a hydroxyl group, or an alkyl group having 1–4 carbon atoms which may have a hydroxyl group. $R^{12}$ is —$CH_2OH$, —COOH, or —$CONH_2$. $R^7$ is hydrogen, a hydroxyl group, or an alkyl group having 1–4 carbon atoms which may have a hydroxyl group. $R^8$ is —$CH_2OH$, —$NH_2$, or —NH—CO—CH($R^{13}$)—$R^{14}$.

$R^{13}$ is hydrogen, a hydroxyl group, or an alkyl group having 1–4 carbon atoms which may have a hydroxyl group. $R^{14}$ is —$CH_2OH$, —$NH_2$, or —NH—CO—CH($R^{15}$)—$R^{16}$. $R^{15}$ is hydrogen, a hydroxyl group, or an alkyl group having 1–4 carbon atoms which may have a hydroxyl group. $R^{16}$ is —$NH_2$ or —$CH_2OH$.

However, the compound which has hydrogen as $R^1$ and $R^3$, a hydroxyl group as $R^4$, and —$CH^2$—CO—NH—CH($R^5$)—$R^6$ as $X^2$, in which $R^5$ is —CH($CH_3$)$_2$ or —CH—($CH_3$)$C_2H_5$, and $R^6$ is —CO—NH—CH($R^9$)—$R^{10}$ in which $R^9$ and $R^{10}$ are —$CH_2OH$, is excluded.

Also, the inventors succeeded in preparation of peptide derivatives described by the following general formula (Ib) from various sphingosine analogues which have the chemical structures similar to the above formula (III), including above sphingosine and phytosphingosine, and found that these showed biological activities similar to those of the compounds described by the above general formula (Ia), resulting in completion of the present invention.

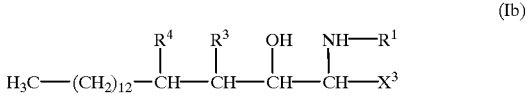

(Ib)

In the formula, $R^1$, $R^3$, and $R^4$ are the same as described above. $X^3$ is the same as $X^2$ of the above formula (Ia).

DETAILED DESCRIPTION OF THE INVENTION

Following is the present invention now described in detail.

Derivatives of sphingosine analogues of the present invention are represented by the general formula (I) described below.

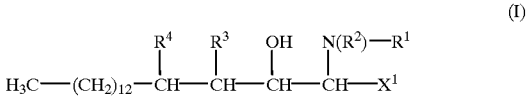

(I)

In the formula, $R^1$ and $R^2$, which are the same or different each other, are hydrogen, alkyl groups having 1–4 carbon atoms, or acyl groups having 2–5 carbon atoms. $R^3$ and $R^4$, which are the same or different each other, are hydrogen or hydroxyl groups; or $R^3$ and $R^4$ make up a covalent bond. $X^1$ is —($CH_2$)$_n$—CO—NH—CH($R^5$)—$R^6$ or —($CH_2$)$_m$—O—CO—CH($R^7$)—$R^8$. The n means an integral number ranging from 0 to 3. $R^5$ is hydrogen, a hydroxyl group, or an alkyl group having 1–4 carbon atoms which may have a hydroxyl group. $R^6$ is —$CH_2OH$, —COOH, —$CONH_2$, or —CO—NH—CH($R^9$)$R^{10}$. $R^9$ is hydrogen, a hydroxyl group, or an alkyl group having 1–4 carbon atoms which may have a hydroxyl group. $R^{10}$ is —$CH_2OH$, —COOH, —$CONH_2$, or —CO—NH—CH($R^{11}$)—$R^{12}$. $R^{11}$ is hydrogen, a hydroxyl group, or an alkyl group having 1–4 carbon atoms which may have a hydroxyl group. $R^{12}$ is —$CH_2OH$, —COOH, or —$CONH_2$. The m means an integral number ranging from 1 to 3. $R^7$ is hydrogen, a hydroxyl group, or an alkyl group having 1–4 carbon atoms which may have a hydroxyl group. $R^8$ is —$CH_2OH$, —$NH_2$, or —NH—CO—CH($R^{13}$)—$R^{14}$. $R^{13}$ is hydrogen, a hydroxyl group, or an alkyl group having 1–4 carbon atoms which may have a hydroxyl group. $R^{14}$ is —$CH_2OH$, —$NH_2$, or —NH—CO—CH($R^{15}$)—$R^{16}$. $R^{15}$ is hydrogen, a hydroxyl group, or an alkyl group having 1–4 carbon atoms which may have a hydroxyl group. $R^{16}$ is —$NH_2$ or —$CH_2OH$.

However, the compound which has hydrogen as $R^1$, $R^2$, and $R^3$, a hydroxyl group as $R^4$, and —$CH_2CO$—NH—CH ($R^5$)—$R^6$ as $X^1$, in which $R^5$ is —CH($CH_3$)$_2$ or —CH($CH_3$) $C_2H_5$, and $R^6$ is —CO—NH—CH($R^9$)—$R^{10}$ in which $R^9$ and $R^{10}$ are —$CH_2OH$, is excluded.

The alkyl group having 1–4 carbon atoms is not limited, and examples are methyl, ethyl, propyl, i-propyl, n-butyl, and t-butyl group.

The acyl group having 2–5 carbon atoms is not limited, and examples are acetyl, propionyl, n-butyryl, and valeryl group.

The derivatives of sphingosine analogues of the present invention are compounds represented by the general formula (I) described above, which includes compounds shown by the above general formula (Ia) or the above general formula (Ib), and the examples are the compounds described in Table 1 shown below.

TKR1785's represented by the above general formula (II), TKR1785-I and TKR1785-II, are prepared by culturing a strain enabling to produce TKR1785's and belonging to Penicillium sp., and isolating them from the cultured broth thereafter. The strain useful to produce TKR1785's described above is exemplified by Penicillium sp. TKR1785 (referred to as "strain TKR1785" thereafter). That is, strain TKR1785 is inoculated into a nutrient medium and cultured in the liquid to obtain TKR1785's described above.

The present inventors deposited the above strain TKR1785 under deposit number of FERM BP-5788 (original date of deposit: May 17, 1995; date of request for transfer to international deposit: Jan. 17, 1997) at National Institute of Bioscience and Human Technology (address; 1-3 Higashi 1-chome, Tsukuba-shi, Ibaraki, Japan (Zip-code 305)).

The culture described above is carried out at 15 to 25° C. preferably, and the incubation for 3 to 11 days usually gives a sufficient production. TKR 1785's accumulated in the cultured product are obtained by purification utilizing their physicochemical and biological properties. When the above purification can be carried out by a method using high performance liquid chromatography, a silica gel chemically-bonded by, for example, octadecyl, octyl, or phenyl group, a polystyrene type porus-polymer gel, or the like is available. The mobile phase includes an aqueous solution of water-soluble organic solvent, for example, aqueous methanol, aqueous acetonitrile, or the like.

The compound represented by the formula (III) to be used for preparation of the compounds represented by the above general formula (I) of the present invention can be prepared from hydrolysis of TKR1785's represented by the above general formula (II). For example, the compound can be obtained by acid hydrolysis of TKR1785-I of the above formula (IIa), e.g. decomposition under the condition of 6N HCl at 110° C. for overnight, which is used for hydrolysis of the peptide bond, followed by neutralizing the reaction solution and being adjusted to alkali. The compound prepared can be isolated by neutralization of the reaction solution again, extraction with an organic solvent such as chloroform, a mixture of chloroform/methanol and the like, and if necessary, further purification using an adsorption chromatography using silica gel or a reversed phase partition chromatography using a chemical-bonded silica gel.

The carboxyl group of the compound represented by the above formula (III) can be converted to an amide by methylation of the carboxyl group followed by ammonolysis, or to a hydroxy group by reduction using lithium aluminum hydride (LiAlH$_4$), sodium borohydride (NaBH$_4$), or the like, resulting in the compound having —CH$_2$OH as Y$^2$ in the above general formula (IIIa).

The lactone represented by the below formula (IV) can be obtained when TKR1785-1 is subjected to acid hydrolysis under the condition similar to that described above, followed by concentration, and then purification.

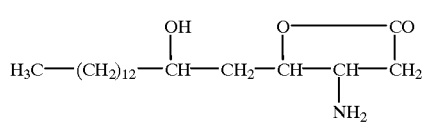

(IV)

The compound, in which R$^3$ and R$^4$ of the compound shown by the above general formula (IIIa) together make a covalent bond, resulting in a double bond between carbon number 4 and carbon number 5, can be easily obtained from the lactone of the above general formula (IV) by dehydration by treating with concentrated sulfuric acid or by reacting with thionyl chloride in pyridine and followed by alkaline hydrolysis.

The compound, in which R$^3$ and R$^4$ of the compound shown by the above general formula (IIIa) together make a covalent bond and its Y$^2$ is COOH, can be prepared by the alkaline hydrolysis of the above compound.

Sphingosine analogues that are able to be used to prepare the derivatives represented by the above general formula (I) of the present invention include not only the compounds shown by the above general formula (IIIa) but also commercially available phytosphingosine, sphingosine, a compound derived from these compounds by hydrogenation of the double bond thereof (sphinganine), a compound derived from these compounds by hydration of the double bond thereof, and a compound derived from these compounds by modification of the terminal hydroxyl group to a caroboxyl group.

To prepare the compounds represented by the above general formula (I), lots of protecting groups used widely for the peptide synthesis can be properly utilized. Such protecting groups, for example, include protecting groups of the amino group, protecting groups of the carboxyl group, and protecting groups of the hydroxyl group.

The above protecting group of the amino group is not particularly restricted, and includes, for example, t-butoxycarbonyl (Boc) group, trichloroethoxycarbonyl (Troc) group, and the like.

The above protecting group of the carboxyl group is not particularly restricted, and includes, for example, phenacyl (Pac) group, benzyl (Bzl) group, and the like.

The above protecting group of the hydroxyl group is not particularly restricted, and includes, for example, Bzl group, acetyl group, methyl group, trimethylsilyl group, and the like.

The above protecting group is respectively removed in need by a known elimination reaction corresponding to each group or its applied elimination reaction, resulting in modification to an objective compound. In the case that protecting groups that can be eliminated by a different condition are used, a selective modification can be easily carried out by performing the above elimination reaction.

For example, in order to prepare a derivative, a compound represented by the general formula (I), using a sphingosine analogue having a carboxyl group at the terminal, the carboxyl group of the sphingosine analogue is linked to the amino group of an amino acid or an amino alcohol by a peptide bond. Methods to make the above peptide bond include, for example, a method which comprises activating the carboxyl group by water-soluble carbodiimide (WSCD) and HOBt, a method which comprises activating the carboxyl group by making carboxyazide by diphenylphosphorylazide, and a method using (benzotriazolyloxy)tris-(dimethylamino)phosphonium fluorophosphate (BOP).

Also, in order to prepare a derivative, a compound represented by the general formula (I), using a sphingosine analogue having a hydroxyl group at the terminal, the hydroxyl group of the sphingosine analogue is linked to the carboxyl group of an amino acid or a carboxylic acid by an ester bond. Methods to make the above ester bond include, for example, a method using N,N'-dicyclohexylcarbodiimide (DCC) in the presence of a catalyst like dimethyl aminopyridine (DMAP) or 4-pyrrolidinopyridine, and the mixed acid anhydride method using 2,4,6-trichlorobenzoyl chloride.

Many kinds of sphingosine analogues including sphingosine and phytosphingosine can be used as the starting material to prepare the derivative represented by the above general formula (I) of the present invention, and an acylated or alkylated product of the sphingosine analogues can also be utilized, because the derivative represented by the above general formula (I) includes a product with the amino group thereof acylated or alkylated.

The above acylation can be carried out by a conventional method using acid anhydride or acid chloride and so forth, and the above alkylation can be performed by a method using sodium hydride and alkyl iodide.

The derivative of sphingosine analogues of the present invention shows the biological activity as shown in Table 2 described below and useful as a pharmaceutical composition.

The derivative of sphingosine analogues of the present invention can each be put to use as such or in the form of a pharmacologically acceptable salt in medicinal applications. There is no particular limitation on the type of pharmacologically acceptable salt. Thus, the salt includes salts of mineral acids such as hydrochloric acid, sulfuric acid, nitric acid, phosphoric acid, hydrofluoric acid, hydrobromic acid, etc., salts of organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc., and salts of alkali metals or alkaline earth metals, such as sodium, potassium, calcium, etc.

To administer the derivative of sphingosine analogues of the present invention or its pharmacologically acceptable salt, as a drug, the derivative of sphingosine analogues of the present invention can be administered either as such or in the form of a pharmaceutical composition containing typically 0.1 to 99.5%, preferably 0.5 to 90% thereof in a pharmaceutically acceptable, non toxic and inert carrier to animals inclusive of humans.

The carrier mentioned above includes solid, semisolid or liquid diluents, fillers, other formulation auxiliaries, etc. and such carriers can be used alone or in combination.

The above-mentioned pharmaceutical composition is preferably administered in unit dosage forms and can be administered orally, parenterally, topically (e.g. transdermally) or rectally. Of course, those pharmaceutical compositions should be administered in dosage forms suited for the respective route of administration.

For administration of the derivative of sphingosine analogues or its pharmacologically acceptable salt of the present invention, as a drug, the dose as an antifungal agent or an antiallergic agent is preferably selected with reference to patient factors such as age and body weight, route of administration, nature and severity of disease, etc. Usually in man, however, the daily dose of the active ingredient for an adult patient is 10 to 2000 mg. While a daily dose lower than the above range may be sufficient in some cases, a dose higher than the range may be required in other cases. When a high dose is used, the daily dosage is preferably administered in several divided doses.

The oral administration mentioned above can be made using solid, powdery, or liquid dosage forms such as bulc powders, powders, tablets, dragees, capsules, drops, sublingual tablets, etc.

For the above-mentioned parenteral administration, liquid unit dosage forms for subcutaneous, intramuscular, or intravenous administration, typically solutions and suspensions, can be employed. These preparations can be manufactured by suspending or dissolving a predetermined amount of the derivative of sphingosine analogue or its pharmacologically acceptable salt of the present invention, in a nontoxic liquid carrier suitable for injection, such as an aqueous medium or an oily medium, and sterilizing the resulting suspension or solution.

The above-mentioned topical administration (e.g. transdermal administration) can be carried out using a variety of topical dosage forms such as liquids, creams, powders, pastes, gels, and ointments. These dosage forms can be manufactured by using a predetermined amount of the derivative of sphingosine analogues of the present invention or a pharmacologically acceptable salt thereof, in combination with one or more of the perfume, coloring agent, filler, surfactant, humectant, emollient, gelatinizer, carrier, preservative, stabilizer, etc., suitable for topical dosage formulations.

The rectal administration can be made using, for example, suppositories each mixing a predetermined amount of the derivative of sphingosine analogues or its pharmacologically acceptable salt of the present invention, with a low-melting solid base such as higher esters, e.g. myristyl palmitate, polyethylene glycol, cacao butter, or a mixture of them.

BEST MODE FOR CARRYING OUT THE INVENTION

The following examples illustrate the present invention in further detail but are not intended to define the scope of the invention.

EXAMPLE 1

Synthesis of Compound (1) from Sphingosine (see Scheme 1)

1) Preparation of N-Boc derivative: Sphingosine (10.0 mg, 33.4 $\mu$mol) was dissolved in dioxane-water (10:1, 300 $\mu$l), Boc—ON (12.7 mg, 50.2 $\mu$mol) and N,N-dhisopropylethylamine (DIEA) (8.8 $\mu$l, 50.2 $\mu$mol) were added thereto at room temperature, and the mixture was stirred for 5 hours. After addition of ethyl acetate, the reaction mixture was washed with 10% aqueous solution of citric acid and then with saturated aqueous solution of NaCl. The ethyl acetate layer was dried over magnesium sulfate, concentrated under reduced pressure, and purified by silica gel thin layer chromatography (TLC) (chloroform-methanol 19: 1), yielding colorless powder of compound (1a) (7.7 mg).

FAB-MS: m/z 400 (M+H)

$^1$H-NMR (500 MHz, DMSO-d$_6$) $\delta$6.18 (d), 5.51 (m), 5.40 (m), 4.76 (d), 4.39 (t), 3.83 (m), 3.49–3.38 (m), 1.93 (m), 1.36–1.20 (m), 0.84 (t), 0.00 (s).

2) Preparation of a TBDMS derivative of the primary alcohol: Compound (1a) (5.7 mg, 14.3 $\mu$mol) was dissolved in dichloromethane (CH$_2$Cl$_2$) (400 $\mu$l), dimethylamiinopyridine (DMAP) (1 mg), triethylamine (NEt$_3$) (2.4 $\mu$l, 17.1 $\mu$mol), and t-butyldimethylsilyl chloride (TBDMS-Cl) (2.4 mg, 15.7 $\mu$mol) were added thereto, and the mixture was stirred at room temperature for 16 hours. The reaction mixture was purified by TLC (chloroform-methanol 100: 1), yielding colorless oil of compound (1b) (6.7 mg).

FAB-MS: m/z 514 (M+H)

$^1$H-NMR (500 MHz, DMSO-d$_6$) δ6.18 (d), 5.50 (m), 5.41 (m), 4.74 (d), 3.82 (m), 3.67 (m), 3.52–3.39 (m), 1.94 (m), 1.35–1.19 (m), 0.84 (m), 0.00 (s).

3) Preparation of an N-Boc derivative of the secondary alcohol: Compound (1b) (2.0 mg, 3.89 µmol) was dissolved in CH$_2$Cl$_2$ (400 µl), DMAP (1 mg) and Boc$_2$O (1.0 mg, 4.67 µmol) were added thereto, and the mixture was stirred for 5.5 hours. After additional addition of Boc$_2$O (2.0 mg, 9.34 µmol), the mixture was further stirred for 17.5 hours. The reaction mixture was purified by TLC (chloroform-methanol 200: 1), yielding colorless oil of compound (1c) (2.4 mg).

FAB-MS: m/z 614 (M+H)

$^1$H-NMR (500 MHz, DMSO-d$_6$) δ6.65 (d), 5.65 (m), 5.41 (m), 4.92 (t), 3.73 (m), 3.52 (m), 1.97 (m), 1.41–1.22 (m), 0.84 (m).

4) Selective removal of TBDMS: Compound (1c) (2.4 mg, 3.91 µmol) in tetrahydrofuran (THF)-acetic acid-water (1:2:1, 1.5 ml) was stirred at room temperature for 17.5 hours. After concentration under reduced pressure, the reaction mixture was purified by TLC (chloroform-methanol 50: 1), yielding colorless oil of compound (1d) (2.0 mg).

FAB-MS: m/z 500 (M+H)

$^1$H-NMR (500 MHz, DMSO-d$_6$) δ6.58 (d), 5.64 (m), 5.39 (m), 4.91 (t), 4.62 (t), 3.66 (m), 3.44 (m), 1.96 (m), 1.40–1.22 (m), 0.84 (t).

5) Coupling of sphingosine and valine: Compound (Id) (3.7 mg, 7.40 µmol), Z—Val—OH (2.8 mg, 11.1 µmol; Z: benzyloxycarbonyl group), and DMAP (0.45 mg, 3.70 µmol) were dissolved in CH$_2$Cl$_2$ (300 µl), DCC (2.3 mg, 11.1 µmol) was added thereto under ice-cooling, and the mixture was stirred for 10 minute and then at room temperature for further 16 hours. After filtration, the reaction mixture was concentrated under reduced pressure, and purified by TLC (chloroform-methanol 100:1), yielding colorless oil of compound (1e) (4.0 mg).

FAB-MS: m/z 733 (M+H)

$^1$H-NMR (500 MHz, DMSO-d$_6$) δ7.66 (d), 7.36–7.28 (m), 6.97 (d), 5.67 (m), 5.55 (d), 5.39 (m), 5.03 (d), 4.88 (t), 3.93 (m), 1.96 (m), 1.71 (m), 1.60 (m), 1.50 (m), 1.38–1.00 (m), 0.84 (m).

6) Synthesis of compound (1f): To a solution of compound (1e) (4.0 mg, 5.46 µmol) in ethyl acetate (20 ml), palladium-black (20 mg) was added, and the mixture was bubbled with hydrogen gas at room temperature for 90 minutes. After filtering off the catalyst, the mixture was concentrated under reduced pressure, resulting in elimination of the Z group and reduction of the double bond, and the compound (1f) (3.8 mg) was obtained.

FAB-MS: m/z 890 (M+H)

$^1$H-NMR (500 MHz, DMSO-d$_6$) δ8.40 (d), 6.99 (d), 5.07 (m), 4.61 (m), 4.33–3.85 (m), 2.07 (m), 1.54–1.22 (m), 0.84 (m).

7) Synthesis of O—Boc-glyceric acid: To a solution of glyceric acid (92.4 mg, 0.871 mmol) in acetone (300 µl), NEt$_3$ (14.6 µl, 1.05 mmol) and phenacyl bromide (PacBr) (203 mg, 1.05 mmol) was added under ice-cooling, and the mixture was stirred for 1 hour and then at room temperature for further 4 hours. After concentration under reduced pressure, the residue was dissolved in ethyl acetate, and washed with water, saturated aqueous solution of sodium hydrogen carbonate and then saturated aqueous solution of NaCl. The ethyl acetate layer was dried over magnesium sulfate, concentrated, and then dried under reduced pressure. The residue was dissolved in ethyl acetate (2 ml), DMAP (36.4 mg, 0.298 mmol) and Boc$_2$O (260.3 mg, 1.193 mmol) were added thereto under ice-cooling, and the mixture was stirred for 5 minutes and for further 4 hours at room temperature. Ethyl acetate was added to the reaction mixture, which was then washed with 10% aqueous solution of citric acid, saturated aqueous solution of NaCl, saturated aqueous solution of sodium hydrogen carbonate, and then saturated aqueous solution of NaCl. The ethyl acetate layer was dried over magnesium sulfate, concentrated under reduced pressure, and purified by TLC (benzene-ethyl acetate 30: 1), yielding the Pac-ester of —Boc-glyceric acid (47.6 mg). This compound (42.8 mg, 0.101 mmol) was dissolved in 90% aqueous solution of acetic acid solution (5 ml), Zn powder (330.2 mg, 5.05 mmol) was added thereto under ice-cooling, and the mixture was stirred for 15 minutes and then 1 hour at room temperature. After filtering off insoluble materials, the reaction mixture was concentrated under reduced pressure, and the resulting residue was dissolved in ethyl acetate, washed with 10% aqueous solution of citric acid, and then saturated aqueous solution of NaCl. The ethyl acetate layer was dried over magnesium sulfate, concentrated under reduced pressure, and purified by TLC (chloroform-methanol-acetic acid 95:5:3), yielding colorless powder of O—Boc-glyceric acid (19.7 mg).

FAB-MS: m/z 305 (M–H)

$^1$H-NMR (500 MHz, DMSO-d$_6$) δ5.05 (m), 4.34 (m), 1.41 (d).

8) Coupling of compound (1f) and glyceric acid: Compound (1f) (3.1 mg, 5.18 µmol) and O—Boc-glyceric acid (2.4 mg, 7.76 µmol) were dissolved in dimethyl formamide (DMF) (500 µl), HOBt (0.84 mg, 6.21 µmol) and WSCD (1.0 µl, 5.69 µmol) were added thereto under ice-cooling, and the mixture was stirred for 3 hours. Ethyl acetate was added to the reaction mixture, which was then washed with 10% aqueous solution of citric acid, saturated aqueous solution of NaCl, saturated aqueous solution of sodium hydrogen carbonate, and then saturated aqueous solution of NaCl. The ethyl acetate layer was dried over magnesium sulfate, concentrated under reduced pressure, the residue obtained was purified by TLC (chloroform-methanol 200:1), and the protected compound (1) was obtained. TFA (500 µl) was added to the product obtained, and the mixture was concentrated under reduced pressure after stirring for 2 hours at room temperature, yielded colorless oil of compound (1) (0.5 mg) shown in Table 1.

FAB-MS: m/z 489 (M+H)

EXAMPLE 2

Synthesis of compound (2)

Compound (1d) (9.3 mg, 18.6 µmol), Fmoc—Val—OH (9.5 mg, 27.9 µmol; 9-fluorenylmethoxycarbonyl group), and DMAP (1.1 mg, 9.31 µmol) were dissolved in CH$_2$Cl$_2$ (500 µl), DCC (5.8 mg, 27.9 µmol) was added thereto under ice-cooling followed by stirring for 45 minutes and then at room temperature for further 19 hours. After filtration and concentration under reduced pressure, the reaction mixture was purified by TLC (chloroform-methanol 200:1), yielding a compound (10.7 mg). To the compound obtained (8.6 mg, 10.5 µmol), 30% piperidine/DMF solution (1 ml) was added under ice-cooling followed by stirring for 30 minutes and then at room temperature for further 1 hour to remove the Fmoc protecting group selectively. The reaction mixture was neutralized by 1N HCl under ice-cooling, concentrated under reduced pressure, and purified by TLC (chloroform-methanol 19:1), yielding the coupling product (4.5 mg) between the protected-sphingosine (1d) and valine (Fmoc—Val—OH).

FAB-MS: m/z 599 (M+H)

The product obtained (5.4 mg, 9.02 μmol) and O—Boc-glyceric acid (4.1 mg, 13.5 μmol) were dissolved in DMF (500 μl), HOBt (1.5 mg, 10.8 μmol) and WSCD (1.8 μl, 9.92 μmol) were added thereto under ice-cooling followed by stirring for 3 hours. Ethyl acetate was added to the reaction mixture, which was then washed with 10% aqueous solution of citric acid, saturated aqueous solution of NaCl, saturated aqueous solution of sodium hydrogen carbonate, and then saturated aqueous solution of NaCl. The ethyl acetate layer was dried over magnesium sulfate, concentrated under reduced pressure, and purified by TLC (chloroform-methanol 100:1), yielding the protected compound (2) (4.3 mg). To the product obtained, TFA (500 μl) was added, and the mixture was stirred for 2 hours at room temperature, concentrated under reduced pressure, yielding colorless oil of compound (2) (1.8 mg) shown in Table 1.

FAB-MS: m/z 487 (M+H)

EXAMPLE 3

Synthesis of compound (3)

Phytosphingosine was used instead of sphingosine used in Example 1 as the starting material, and gave colorless oil (1.5 mg) of compound (3) shown in Table 1 by steps similar to those for synthesis of compound (1) in Example 1.

FAB-MS: m/z 505 (M+H)

Reference Example 1

Synthesis of TKR1785-I

1) Preparation of isopropylidene derivative of compound (III). Compound (III) (5.0 mg, 14.5 μmol) was suspended in acetone (900 μl), and acetone dimethylacetal (150 μl) and dl-camphor sulfonic acid (1 mg) were added thereto followed by stirring for 1 hour at room temperature. The reaction mixture was neutralized with NEt$_3$ (10 μl) and concentrated under reduced pressure. The residue was purified by TLC [the lower layer of a mixture of chloroform-methanol-water (8:3:1)], and gave the objective compound (amount 2.8 mg, yield 51%) as colorless oil.

FAB-MS: m/z 386 (M+H)

2) Preparation of the trichloroethoxycarbonyl (Troc) derivative: The compound obtained in 1) (1.4 mg, 3.6 μmol) was dissolved in pyridine (100 μl), and trichloroethoxycarbonyl chloride (1.5 μl, 10.9 μmol) was added thereto under ice-cooling followed by stirring for 30 min. under ice-cooling and then for 1 hour at room temperature. The reaction mixture was purified by TLC (the lower layer of a mixture of chloroform-methanol-water, 8:3:1), and gave the objective compound (amount 1.0 mg, yield 42%) as colorless powder.

FAB-MS: m/z 734 (M–H)

3) Synthesis of TKR1785-I. The compound obtained in 2) described above, Troc derivative (5.0 mg, 6.0 μmol) and HCl.H$_2$N—CH(CH(CH$_3$)$_2$)—CONH—CH(CH$_2$OBzl)—CH$_2$OBzl (4.8 mg, 12.0 μmol), which was separately prepared using Boc—NH—CH(CH$_2$OH)CH$_2$OBzl as the starting material, were dissolved in CH$_2$Cl$_2$ (100 μl), and appropriate amount of WSCD and HOBt were added thereto as described in Examples 1–8). The mixture was stirred for 30 min. under ice-cooling and stirred overnight at room temperature. The reaction mixture was purified by TLC (chloroform-methanol 19:1), and gave the objective compound (amount 3.9 mg, yield 60%) as colorless powder.

FAB-MS: m/z 1088 (M+H)

The product (3.9 mg, 3.6 μmol) was dissolved in methanol (3 ml), and palladium-black (15 mg) was added thereto followed by stirring at room temperature for 90 minutes with bubbling of hydrogen gas. After filtering off the catalyst from the reaction mixture, the filtrate was concentrated under reduced pressure, yielding colorless powder.

FAB-MS: m/z 908 (M+H)

Then, the product obtained was dissolved in 90% acetic acid aqueous solution (2 ml), and Zn powder (100 mg) was added thereto under ice-cooling followed by stirring for 10 minutes under ice-cooling and for 2 hours at room temperature. After filtering off insoluble materials, the filtrate was concentrated under reduced pressure, yielding TKR1785-I (amount 1.1 mg) as colorless powder.

FAB-MS: m/z 518 (M+H)

EXAMPLE 4

Synthesis of Compound (4)

1) Oxidation of Compound (1d): Pyridinium dichromate (12.8 mg, 34 μmol) suspended in DMF (50 μl) was added to a solution of compound (1d) (4.8 mg, 9.6 μmol) in DMF (50 μl) followed by stirring for 24 hours at room temperature. After addition of water, the mixture was stirred for 10 minutes, extracted with chloroform, and the extract was concentrated under reduced pressure. The residue was purified by TLC, yielding colorless solid (amount 2.5 mg, yield 51%).

FAB-MS: m/z 514 (M+H)

2) Synthesis of Compound (4): The compound (2.0 mg, 3.9 lμmol) obtained in the above 1), and HCl.H$_2$N—CH(CH(CH$_3$)$_2$)—CONH—CH(CH$_2$OTroc)—CH$_2$OTroc (4.5 mg, 7.8 μmol), which was separately prepared using —Boc—NH—CH(CH$_2$OH)CH$_2$OH as the starting material, were coupled similarly to Examples 1–8). Purification of the reaction mixture by TLC gave the protecting derivative of compound (4) (amount 2.8 mg, yield 70%) as colorless powder.

FAB-MS: m/z 1037 (M+H)

This compound obtained (2.8 mg, 2.7 μmol) was dissolved in 90% acetic acid aqueous solution (2 ml), and zinc powder (100 mg) was added thereto under ice-cooling followed by stirring for 10 minutes under ice-cooling and for further 1 hour at room temperature. After filtering off insoluble materials, the filtrate was concentrated under reduced pressure, yielding colorless powder.

FAB-MS: m/z 687 (M+H)

Thereafter, to the compound obtained, trifluoroacetic acid (TFA) (500 μl) was added under ice-cooling. The mixture was left for 1 hour under ice-cooling, and concentrated under reduced pressure, yielding the compound (4) (amount 1.0 mg) as colorless powder.

FAB-MS: m/z 487 (M+H)

EXAMPLE 5

Synthesis of Compound (5)

Compound (1d) (4.0 mg, 8.00 μmol), O—Boc-glyceric acid (3.0 mg, 12.0 μmol), and DMAP (0.49 mg, 4.00 μmol) were dissolved in CH$_2$Cl$_2$ (300 μl), and DCC (2.5 mg, 12.0 μmol) wad added thereto under ice-cooling followed by stirring for 10 minutes and then for additional 14 hours at room temperature. After filtration, the reaction mixture was concentrated under reduced pressure and purified by TLC (chloroform-methanol, 200:1). TFA (500 μl) was added to the compound obtained, and after stirring for 2 hours at room temperature the mixture was concentrated under reduced pressure, yielding compound (5) (1.4 mg) shown in Table 1 as colorless oil.

FAB-MS: m/z 388 (M+H)

EXAMPLE 6

To the coupling compound (4.4 mg, 7.3 μmol) of the protected-sphingosine (1d) obtained in Example 2 and valine, TFA (500 μl) was added followed by stirring for 3 hours at room temperature. The reaction mixture was concentrated under reduced pressure, yielding the compound (6) (2.3 mg) shown in Table 1 as colorless oil.

FAB-MS: m/z 399 (M+H)

EXAMPLE 7

Synthesis of Compound (7)

The carboxyl group of compound (III) was reduced by LiAlH$_4$, yielding a primary OH, and followed by changing to a N-Boc derivative. Then the primary OH was protected by a t-butyldimethylsilyl (TBDMS) group, the secondary OH was by O—Boc group, and then the TBDMS of the primary OH was removed, yielding H$_3$C—(CH$_2$)$_{12}$—CH(OBoc)—CH$_2$—CH(OBoc)—CH(NBBoc)—CH$_2$—CH$_2$OH. This compound (3.5 mg, 5.5 μmol) and Fmoc—Ile—OH (2.5 mg, 7.1 μmol) were used as the starting materials to be coupled in the similar way to Example 2, and Fmoc and Boc were removed from the product, yielding compound (7) (1.7 mg) shown in Table 1 as colorless oil.

FAB-MS 445 (M+H)

EXAMPLE 8

Synthesis of Compound (8)

Boc—Ser(Bzl)-ol (300 mg, 1.07 mmol) was dissolved in DMF (2 ml), and NaH (50% oil suspension; 77.3 mg, 1.61 mmol) was added under ice-cooling thereto followed by stirring for 30 minutes. After addition of benzyl bromide (165 μl, 1.39 mmol), the mixture was stirred for 10 minutes under ice-cooling, and stirred for 1 hour at room temperature. Aqueous solution of 10% citric acid was added to the reaction mixture, and ethyl acetate added for extraction. The ethyl acetate layer was washed with saturated aqueous solution of sodium hydrogen carbonate, then saturated aqueous solution of NaCl, dried over magnesium sulfate, and concentrated under reduced pressure, yielding the dibenzyl derivative of Boc—Ser-ol. The Boc group of this compound was removed and sequentially coupled to Boc—Val—OH and then to Boc—Ala—OH. The Boc group of the product was removed. The product (9.5 mg, 16.9 μmol) obtained was coupled to the compound (5.7 mg, 11.1 μmol) obtained in the step 1) of the synthesis of compound (4), and the protecting groups were removed by an ordinary method, yielding compound (8) (0.5 mg) shown in Table 1 as colorless oil.

FAB-MS: m/z 559 (M+H)

EXAMPLE 9

Synthesis of Compound (9)

Compound (1) (2.0 mg, 4.1 μmol) was dissolved in methanol (200 μl), and acetic anhydride (60 μl) was added thereto under ice-cooling. The mixture was stirred for 18 hours at room temperature. The reaction mixture was concentrated under reduced pressure and the residue was purified by TLC (developed and eluted with a solution of chloroform-methanol, 19:1), yielding compound (9) (1.5 mg) shown in Table 1 as colorless oil.

FAB-MS: m/z 531 (M+H)

TABLE 1

| Compounds | $R^1$ | $R^2$ | $R^3$ | $R^4$ | $X^1$ |
|---|---|---|---|---|---|
| (1) | H | H | H | H | —CH$_2$O—CO—CH(CH(CH$_3$)$_2$)—NH—CO—CH(OH)—CH$_2$OH |
| (2) | H | H | — (double bond) | — | —CH$_2$O—CO—CH(CH(CH$_3$)$_2$)—NH—CO—CH(OH)—CH$_2$OH |
| (3) | H | H | OH | H | —CH$_2$O—CO—CH(CH(CH$_3$)$_2$)—NH—CO—CH(OH)—CH$_2$OH |
| (4) | H | H | — (double bond) | — | —CO—NH—C(CH(CH$_3$)$_2$)H—CO—NH—C(CH$_2$OH)H—CH$_2$OH |
| (5) | H | H | — (double bond) | — | —CH$_2$O—CO—CH(OH)—CH$_2$OH |
| (6) | H | H | — (double bond) | — | —CH$_2$O—CO—CH(CH(CH$_3$)$_2$)—NH$_2$ |
| (7) | H | H | H | OH | —CH$_2$—CH$_2$O—CO—CH(CH(CH$_3$)—CH$_2$CH$_3$)—NH$_2$ |

TABLE 1-continued

| Compounds | R$^1$ | R$^2$ | R$^3$ | R$^4$ | X$^1$ |
|---|---|---|---|---|---|
| (8) | H | H | H | H | —CO—NH—CH(CH$_3$)—CO—NH—CH(CH(CH$_3$)$_2$)—CO—NH—CH(CH$_2$OH)—CH$_2$OH |
| (9) | —CO—CH$_3$ | H | H | H | —CH$_2$O—CO—CH(CH(CH$_3$)$_2$)—NH—CO—CH(OH)—CH$_2$OH |

Test Example
Biological Characteristics

Antifungal activity and immunosuppressive activity of the product derivatives of sphingosine analogues were investigated by the following method. The results are set forth in Table 2.

Measurement of Antifungal Activity

The test microorganism used was Cryptococcus neoformans TIMM 0354. YNBG liquid medium (Difco yeast nitrogen base 0.67%, glucose 1%) was used and the minimum growth inhibitory concentration (SIC) was determined after culturing for 2 days at 30° C. in the presence of the serial two-fold dilution of the compound. The minimum growth sub-inhibitory concentration (μg/ml) was determined as the minimum concentration causing partial growth inhibition of the microorganism and also shown in Table 2 in parentheses.

Measurement of Immunosuppressive Activity

We measured inhibitory activity of mixed lymphocytes reaction (MLR) and determined the 50% inhibitory activity. Lymphocytes used are T cells from spleen cells of C57BL/6 mice and BALB/c mice.

TABLE 2

| | Antifungal activity MIC (μg/ml) | Immunosuppressive activity IC50 (μg/ml) |
|---|---|---|
| Compound (1) | 50 (25) | 3.25 |
| Compound (2) | 25 (12.5) | 1.86 |
| Compound (5) | 50 (25) | 5 |
| Compound (6) | 50 (25) | 1.55 |
| Compound (8) | (50) | 0.44 |

TABLE 3

Scheme 1

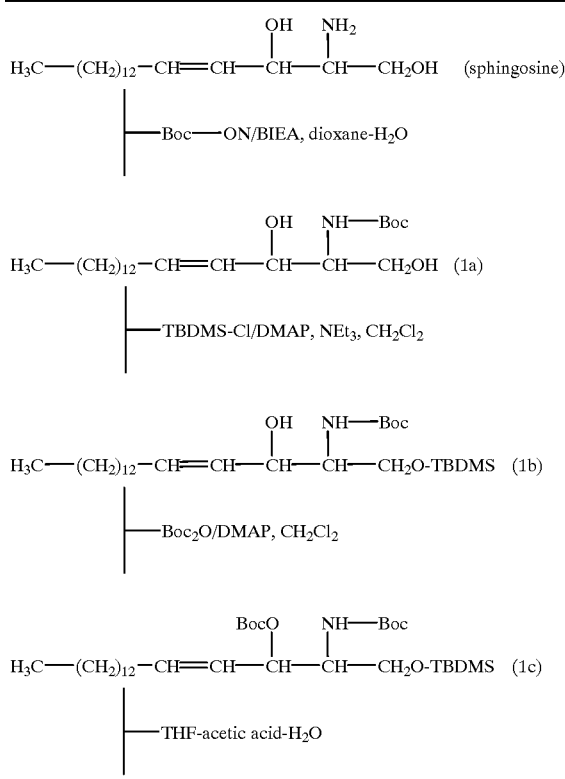

TABLE 3-continued

Scheme 1

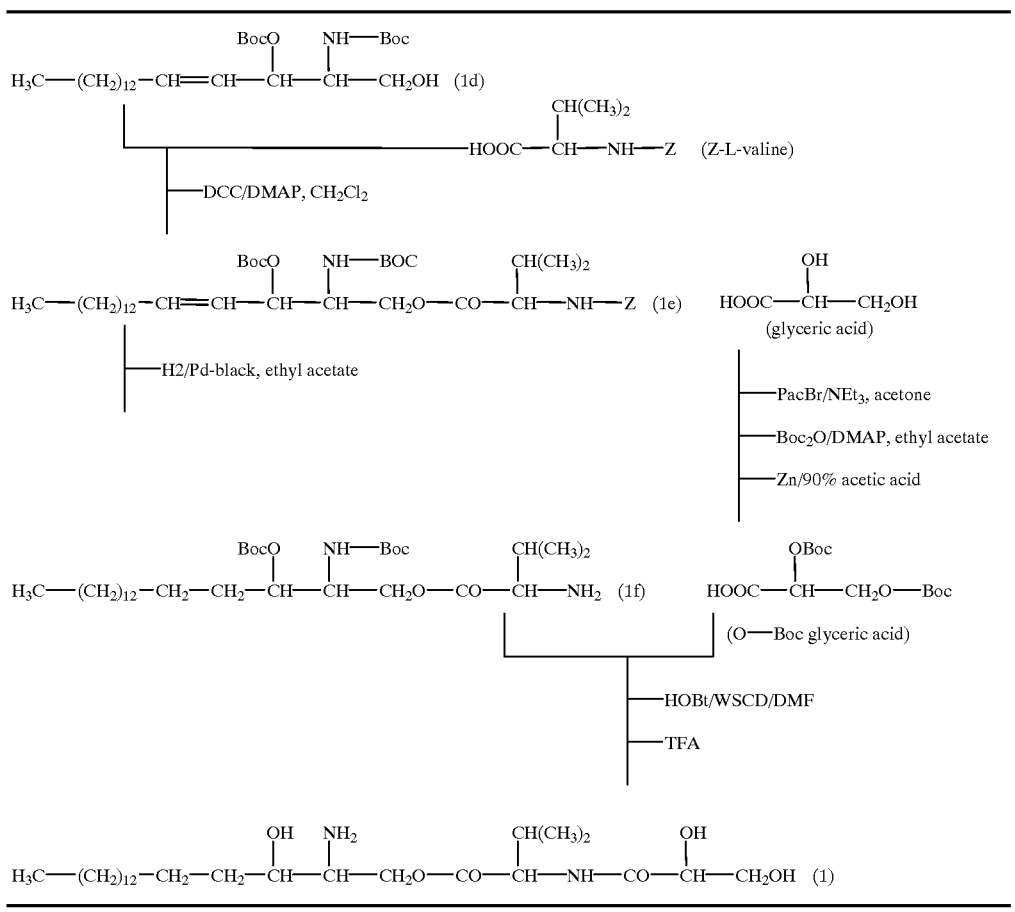

INDUSTRIAL APPLICABILITY

The derivatives of sphingosine analogues of the present invention consist of the composition described above, and have antifungal activity and immunomodulatory activity including immunosuppression. Thus they can be used as antifungal agents and immunoregulatory agents.

What is claimed is:

1. Derivatives of sphingosine analogues represented by the general formula (I) described below.

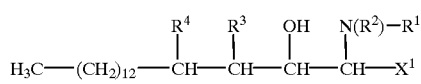

(I)

In the formula, $R^1$ and $R^2$, which are the same or different each other, are hydrogen, alkyl groups having 1–4 carbon atoms, or acyl groups having 2–5 carbon atoms. $R^3$ and $R^4$, which are the same or different each other, are hydrogen or hydroxyl groups; or $R^3$ and $R^4$ make up a covalent bond. $X^1$ is —(CH$_2$)$_n$—CO—NH—CH(R$^5$)—R$^6$ or —(CH$_2$)$_m$—O—CO—CH(R$^7$)—R$^8$. The n means an integral number ranging from 0 to 3. $R^5$ is hydrogen, a hydroxyl group, or an alkyl group having 1–4 carbon atoms which may have a hydroxyl group. $R^6$ is —CH$_2$OH, —COOH, —CONH$_2$, or —CO—NH—CH(R$^9$)—R$^{10}$. $R^9$ is hydrogen, a hydroxyl group, or an alkyl group having 1–4 carbon atoms which may have a hydroxyl group. $R^{10}$ is —CH$_2$OH, —COOH, —CONH$_2$, or —CO—NH—CH(R$^{11}$)—R$^{12}$. $R^{11}$ is hydrogen, a hydroxyl group, or an alkyl group having 1–4 carbon atoms which may have a hydroxyl group. $R^{12}$ is —CH$_2$OH, —COOH, or —CONH$_2$. The m means an integral number ranging from 1 to 3. $R^7$ is hydrogen, a hydroxyl group, or an alkyl group having 1–4 carbon atoms which may have a hydroxyl group. $R^8$ is —CH$_2$OH, —NH$_2$, or —NH—CO—CH(R$^{13}$)—R$^{14}$. $R^{13}$ is hydrogen, a hydroxyl group, or an alkyl group having 1–4 carbon atoms which may have a hydroxyl group. $R^{14}$ is —CH$_2$O, —NH$_2$, or —NH—CO—CH(R$^{15}$)R$^{16}$. $R^{15}$ is hydrogen, a hydroxyl group, or an alkyl group having 1–4 carbon atoms which may have a hydroxyl group. $R^{16}$ is —NH$_2$ or —CH$_2$OH.

The compound which has hydrogen as $R^1$, $R^2$, and $R^3$, a hydroxyl group as $R^4$, and —CH$_2$—CO—NH—CH(R$^5$)—R$^6$ as $X^1$, in which $R^5$ is —CH(CH$_3$)$_2$ or —CH—(CH$_3$)C$_2$H$_5$, and $R^6$ is —CO—NH—CH(R$^9$)—R$^{10}$ in which $R^9$ and $R^{10}$ are —CH$_2$OH, is excluded.

2. Pharmaceutical compositions comprising the derivative of sphingosine analogue as claimed in claim 1 or its pharmacologically acceptable salt as an effective ingredient.

* * * * *